United States Patent [19]

Sone et al.

[11] 4,354,468
[45] Oct. 19, 1982

[54] SYSTEM FOR FEEDBACK CONTROL OF AIR/FUEL RATIO IN IC ENGINE WITH SUBSYSTEM TO CONTROL CURRENT SUPPLY TO OXYGEN SENSOR

[75] Inventors: Kohki Sone, Tokyo; Okamura Kenji, Zushi, both of Japan

[73] Assignee: Nissan Motor Company, Limited, Yokohama, Japan

[21] Appl. No.: 193,716

[22] Filed: Oct. 3, 1980

[30] Foreign Application Priority Data

Oct. 9, 1979 [JP] Japan ................................. 54-130602

[51] Int. Cl.³ .............................................. F02D 5/00
[52] U.S. Cl. .................................... 123/440; 123/489; 123/492
[58] Field of Search ............... 123/440, 489, 492, 493; 60/276, 285

[56] References Cited

U.S. PATENT DOCUMENTS 4,103,649  8/1978  Matumoto et al. ................... 123/440
4,129,099  12/1978  Howarth ............................ 60/276 X
4,207,159  6/1980  Kimura et al. .................... 204/195 S
4,248,196  2/1981  Toelle ............................. 123/440 X

FOREIGN PATENT DOCUMENTS 1490803  11/1977  United Kingdom .
1536718  12/1978  United Kingdom .

Primary Examiner—William A. Cuchlinski, Jr.
Attorney, Agent, or Firm—Schwartz, Jeffery, Schwaab, Mack, Blumenthal & Koch

[57] ABSTRACT

A system for feedback control of air/fuel ratio in an IC engine, utilizing a recently developed oxygen-sensitive device which is provided with a heater and disposed in exhaust gas to provide a feedback signal. This device has a porous solid electrolyte layer with a measurement electrode layer on one side and a reference electrode on the other side facing a substrate. There is a circuit to supply a heating current to the heater and force a DC current to flow in the solid electrolyte layer to cause migration of oxygen ions through the solid electrolyte toward the reference electrode to thereby establish a reference oxygen partial pressure on the reference side of the solid electrolyte layer. To prevent lowering of this oxygen partial pressure while the engine is operated under a high-load condition and the feedback control is discontinued to feed the engine with a fuel-enriched mixture, the control system includes operating condition sensor means and switching means to interrupt the supply of the current to the heater in response to a command signal from the sensor means and, optionally, current regulating means to increase the intensity of current flowing in the solid electrolyte also in response to the command signal.

6 Claims, 4 Drawing Figures

SYSTEM FOR FEEDBACK CONTROL OF AIR/FUEL RATIO IN IC ENGINE WITH SUBSYSTEM TO CONTROL CURRENT SUPPLY TO OXYGEN SENSOR

BACKGROUND OF THE INVENTION

1. Field of the Invention

This invention relates to a system for feedback control of the air/fuel mixture ratio in an internal combustion engine. The system includes an air/fuel ratio detector having an oxygen-sensitive element of an oxygen concentration cell type operated with the supply of a DC current to establish a reference oxygen partial pressure in the element and is further provided with an electric heater to ensure the proper functioning of the element. More particularly, the invention relates to a sub-system to control a heating current to the heater of the oxygen-sensitive element preferably together with controlling the intensity of the current for establishing the reference oxygen partial pressure.

2. Background of the Invention

In recent internal combustion engines and particularly in automotive engines, it has become popular to control the air/fuel mixture ratio precisely to a predetermined optimal value by performing feedback control with the dual object of improving the efficiencies of the engines and reducing the emission of noxious or harmful substances contained in exhaust gases.

For example, in an automotive engine system including a catalytic converter which is provided in the exhaust passage and which contains a so-called three-way catalyst that can catalyze both the reduction of nitrogen oxides and oxidation of carbon monoxide and unburned hydrocarbons, it is desirable to control the air/fuel mixture ratio at a stoichiometric ratio because the catalyst exhibits the highest conversion efficiencies in an exhaust gas produced by the combustion of a stoichiometric air-fuel mixture, and also because the employment of a stoichiometric mixing ratio is favorable for realizing high mechanical and thermal efficiencies in the engine. It is already known to practice feedback control of the air/fuel ratio in such an engine system by using a sort of oxygen sensor, which is installed in the exhaust passage upstream of the catalytic converter together with a device that provides an electrical feedback signal indicative of the air/fuel ratio of an air-fuel mixture actually supplied to the engine. Based on this feedback signal, a control circuit commands a fuel-supplying apparatus such as electronically controlled fuel injection valves to control the rate of fuel feed to the engine so as to nullify or minimize deviations of the actual air/fuel ratio from the intended stoichiometric ratio.

Usually the above mentioned oxygen sensor is of an oxygen concentration cell type utilizing an oxygen ion conductive solid electrolyte, such as zirconia stabilized with calcia, and conventionally the sensor is constituted of a solid electrolyte layer in the shape of a tube closed at one end, a measurement electrode layer porously formed on the outer side of the solid electrolyte tube and a reference electrode layer formed on the inner side of the tube. When there is a difference in oxygen partial pressure between the reference electrode side and measurement electrode side of the solid electrolyte tube, this sensor generates an electromotive force between the two electrode layers. As an air/fuel ratio detector for the above mentioned purpose, the measurement electrode is exposed to an engine exhaust gas while the reference electrode on the inside is exposed to atmospheric air utilized as the source of a reference oxygen partial pressure. In this state the magnitude of the electromotive force generated by this sensor exhibits a great and sharp change between a maximally high level and a very low level each time when the air/fuel ratio of a mixture supplied to the engine changes across the stoichiometric ratio. Accordingly it is possible to produce a fuel feed rate control signal based on the result of a comparison of the output of the oxygen sensor with a reference voltage which has been set at the middle of the high and low levels of the sensor output.

However, this type of oxygen sensor has disadvantages such as significant temperature dependence of its output characteristics, necessity of using a reference gas such as air, difficulty in reducing the size and insufficiency of mechanical strength.

To eliminate such disadvantages of the conventional oxygen sensor, U.S. Pat. No. 4,207,159 discloses an advanced device comprising an oxygen-sensitive element in which an oxygen concentration cell is constituted of a flat and microscopically porous layer of solid electrolyte, a measurement electrode layer porously formed on one side of the solid electrolyte layer and a reference electrode layer formed on the other side on a base plate or substrate such that the reference electrode layer is sandwiched between the substrate and the solid electrolyte layer and macroscopically shielded from the environmental atmosphere. Each of the three layers on the substrate can be formed as a thin, film-like layer. This device does not use any reference gas. Instead, a DC power supply means is connected to the oxygen-sensitive element so as to force a constant DC current (e.g. of a current intensity of about 10 $\mu A$) to flow through the solid electrolyte layer between the two electrode layers to thereby cause migration of oxygen ions through the solid electrolyte layer in a selected direction and, as a consequence, establish a reference oxygen partial pressure at the interface between the solid electrolyte layer and the reference electrode layer, while the measurement electrode layer is made to contact an engine exhaust gas. Where the current is forced to flow through the solid electrolyte layer from the reference electrode layer toward the measurement electrode layer, there occur ionization of oxygen contained in the exhaust gas at the measurement electrode and a migration of negatively charged oxygen ions through the solid electrolyte layer toward the reference electrode. The rate of supply of oxygen in the form of ions to the reference electrode is primarily determined by the intensity of the current. The oxygen ions arriving at the reference electrode layer are deprived of electrons and turn into oxygen molecules to result in an accumulation of gaseous oxygen on the reference electrode side of the concentration cell. However, a portion of the accumulated oxygen molecules diffuse outwardly through the microscopical gas passages in the solid electrolyte layer. Therefore, it is possible to maintain a constant and relatively high oxygen partial pressure which can serve as a reference oxygen partial pressure at the interface between the reference electrode layer and the solid electrolyte layer by the employment of an appropriate current intensity with due consideration of the microscopical structure and activity of the solid electrolyte layer. Generated between the reference and measurement electrode layers of this oxygen-sensitive element is an electromotive force, the magnitude of which is related to the composition of the exhaust gas and the air/fuel ratio of a mixture from which the exhaust gas is produced. Also, it is possible to operate this oxygen-sensitive element by forcing a current to flow therein from the measurement electrode layer toward the reference electrode layer. In this case a constant and relatively low oxygen partial pressure can be maintained at the interface between the reference electrode layer and the solid electrolyte layer.

To supply a DC current of an accurately constant intensity, use is made of a constant current supply circuit including conventional electronic control means.

Devices such as that described in U.S. Pat. No. 4,207,159 have the advantages that it is unnecessary to use any reference gas, it can be made in a very small size and has good resistance to mechanical shocks and vibrations.

In practical applications it becomes necessary to provide this device (also conventional oxygen sensors of the solid electrolyte concentration cell type) with an electric heater because the activity of the solid electrolyte layer in the device becomes unsatisfactorily low while the temperature of the oxygen-sensitive element is relatively low, e.g. is below about 400° C. Therefore, the oxygen-sensitive element installed in an engine exhaust system becomes ineffective as an air/fuel ratio detector while the engine discharges a relatively low temperature exhaust gas if the element should be heated solely by the heat of the exhaust gas. The electric heater is usually attached to, or embedded in, the substrate of the oxygen-sensitive element.

In automotive engines provided with an air/fuel ratio feedback control system as mentioned hereinbefore utilizing an air/fuel ratio detector according to U.S. Pat. No. 4,207,159, it is usual to temporarily release the air/fuel ratio from feedback control while the engine is operated under certain high-load conditions as typified by a full-throttle or nearly full-throttle accelerating condition in order to supply a fuel-enriched mixture to the engine and attain good accelerating performance. Under such conditions, there occurs considerable lowering of the oxygen concentration in the exhaust gas and a considerable rise in the exhaust gas temperature. Then, there occurs an unfavorable phenomenon in that the magnitude of a reference oxygen partial pressure on the reference electrode side of the oxygen-sensitive element decreases considerably even though the supply of a current of a constant intensity to this element is continued. This phenomenon occurs because, although the migration of oxygen ions through the solid electrolyte layer toward the reference electrode layer by the effect of the constant current flowing in the solid electrolyte layer continues, the outward diffusion of gaseous oxygen from the reference electrode through the solid electrolyte layer into the exhaust gas of a lowered oxygen concentration augments. Such a deviation of the reference oxygen partial pressure from an initially intended value offers little problem so long as the feedback control of air/fuel ratio is discontinued. However, when the feedback control is resumed the lowered reference oxygen partial pressure does not instantly revert to the initially intended value but gradually rises to this value, meaning that the recovery of the initially intended level of reference oxygen partial pressure takes a relatively long period of time compared with the frequencies of the feedback signal produced by the air/fuel ratio detector and the control signal supplied to the fuel system. Therefore, during this time period it becomes impossible to accurately control the air/fuel ratio to a predetermined ratio such as a stoichiometric ratio.

SUMMARY OF THE INVENTION

It is an object of the present invention to provide a system for feedback control of air/fuel ratio in an internal combustion engine, which utilizes an oxygen-sensitive air/fuel ratio detector of the type disclosed in U.S. Pat. No. 4,207,159 provided with an electric heater and disposed in an exhaust passage and which comprises a supplementary control loop to preclude undesirable lowering of a reference oxygen partial pressure established in the air/fuel ratio detector during temporary discontinuance of the feedback control to operate the engine under a high-load condition with an intentionally fuel-enriched mixture.

A feedback control system according to the invention comprises an electrically controllable fuel supply means provided in the intake system of an internal combustion engine; an air/fuel ratio detector which is disposed in the exhaust passage for the engine and which has an oxygen-sensitive element of a concentration cell type comprising a substrate, a microscopically porous reference electrode layer formed on the substrate, a microscopically porous layer of an oxygen ion conductive solid electrolyte formed on the substrate so as to cover the reference electrode layer substantially entirely and a microscopically porous measurement electrode layer formed on the solid electrolyte layer and an electric heater; and a fuel feed control means for providing a control signal to the fuel supplying means to control the rate of fuel feed to the engine so as to maintain a predetermined air/fuel ratio by utilizing the output of the air/fuel ratio detector as a feedback signal. This control system further comprises a sub-system to supply a heating current to the heater of the air/fuel ratio detector and force a DC current of a predetermined intensity to flow through the solid electrolyte layer of the oxygen-sensitive element from the reference electrode layer toward the measurement electrode layer to cause migration of oxygen ions through the solid electrolyte layer from the measurement electrode layer toward the reference electrode layer to thereby establish a reference oxygen partial pressure at the interface between the reference electrode layer and the solid electrolyte layer. This sub-system comprises operating condition detecting means for producing a command signal while the operation of the fuel feed control means is temporarily discontinued to release the air/fuel ratio from the feedback control and the engine is operated under such a condition as causes a significant lowering of the concentration of oxygen in the exhaust gas, and an electrically controllable switch means for interrupting the supply of the heating current to the heater of the air/fuel ratio detector while the operating condition detecting means produces the command signal.

As will be understood from the above statement, in this control system the heater provided to the oxygen-sensitive air/fuel ratio detector is made ineffective while the engine is operated under a high-load condition with the feed of a fuel-enriched mixture by temporarily releasing the air/fuel ratio from the feedback control. Therefore, the solid electrolyte layer in the oxygen-sensitive element undergoes a lowering of its temperature and, hence, a lowering of its activity. (As is well known, the activity of an oxygen ion conductive solid electrolyte depends greatly on the temperature.) As a consequence, the rate of diffusion of oxygen from the reference electrode layer through the solid electrolyte layer into the exhaust gas lowers considerably despite lowering of the concentration of oxygen in the exhaust gas. Therefore, the magnitude of the reference oxygen partial pressure established on the reference electrode side of the solid electrolyte layer does not significantly lower during the temporary discontinuance of the feedback control of air/fuel ratio, and, accordingly, when the feedback control is resumed the output of the air/fuel ratio detector serves as a correct feedback signal and enables control of the air/fuel ratio accurately to the predetermined ratio without the need of awaiting the lapse of a substantial length of time.

Preferably, the aforementioned sub-system comprises a current-intensity control means for temporarily increasing the intensity of the DC current flowing in the solid electrolyte layer of the air/fuel ratio detector from the predetermined intensity while the aforementioned command signal is produced and accordingly the supply of the heating current to the heater is interrupted. Since an increase in the current intensity is effective for augmenting the migration of oxygen ions through the solid electrolyte layer toward the reference electrode layer, it accordingly compensates for the tendency of the reference oxygen partial pressure to decrease. For example, this current-intensity control means can be embodied is a combination of a current-intensity-determining resistance and an electrically controllable on-off type switching device which causes short-circuiting of a part of the resistance in response to the command signal.

DETAILED DESCRIPTION OF THE INVENTION

Figure 1:
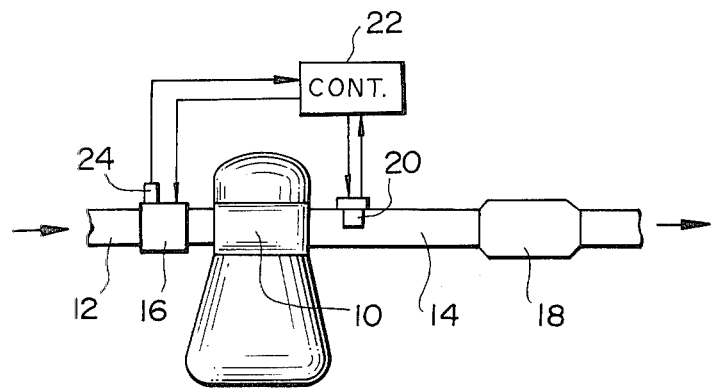
FIG. 1 is a diagrammatic presentation of an internal combustion engine system including an air/fuel ratio control system with which the present invention is concerned.

In FIG. 1, reference numeral 10 indicates an internal combustion engine, which may be an automotive engine, provided with an induction passage 12 and an exhaust passage 14. Indicated at 16 is an electrically or electronically controlled fuel-supplying apparatus such as electronically controlled fuel injection valves. A catalytic converter 18 occupies a section of the exhaust passage 14 and contains therein a conventional three-way catalyst.

To perform feedback control of the fuel-supplying apparatus 16 with the aim of constantly supplying a stoichiometric air-fuel mixture to the engine 10 during its normal operation for thereby allowing the three-way catalyst in the converter 18 to exhibit its best conversion efficiencies, an air/fuel ratio detector 20 (which is an oxygen sensor in principle) is disposed in the exhaust passage 14 at a section upstream of the catalytic converter 18. An electronic control unit 22 receives the output of the air/fuel ratio sensor 20 and provides a control signal to the fuel-supplying apparatus 16 based on the magnitude of a deviation of the actual air/fuel ratio indicated by the output of the sensor 20 from the stoichiometric air/fuel ratio. As will be illustrated hereinafter in FIG. 2, the air/fuel ratio detector 20 comprises an oxygen-sensitive element of the type requiring the supply of a DC current thereto in order to establish a reference oxygen partial pressure therein, and an electric heater is provided to this element. The control unit 22 includes a circuit to supply a heating current to the heater in the air/fuel ratio detector 20 and a constant DC current to the oxygen-sensitive part of this detector 20.

According to the present invention, this current-supplying circuit is modified and afforded the function of temporarily interrupting the supply of a heating current to the heater in the air/fuel ratio detector 20 while the engine 10 is operated under high-load conditions where the feedback control of air/fuel ratio is temporarily discontinued and the rate of fuel feed from the apparatus 16 to the engine 10 is so greatly augmented as to cause a considerable deviation of the air/fuel ratio from the stoichiometric ratio toward the rich side and, as a consequence, a significant lowering of the oxygen concentration in the exhaust gas. To detect such operating conditions, the control system of FIG. 1 includes operating condition detecting means 24 is put into the modified current-supplying circuit in the control unit 22. Preferably the current-supplying circuit is additionally afforded the function of temporarily increasing the intensity of the current being supplied to the air/fuel ratio detector 20 for the establishment of a reference oxygen partial pressure while the supply of the heating current is interrupted. These functions of the current-supplying circuit according to the invention and the operating condition detecting means 24 will later be described more in detail.

Figure 2:
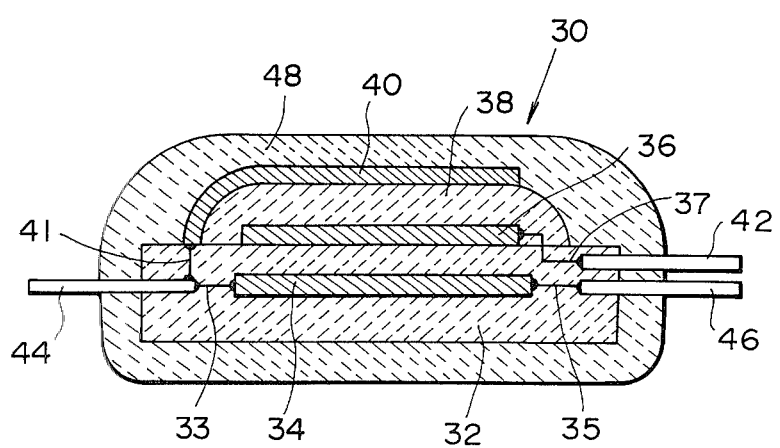
FIG. 2 is a schematic and sectional view of an oxygen-sensitive element of an air/fuel ratio detector employed in the present invention.

FIG. 2 shows an exemplary construction of an oxygen-sensitive element 30 of the oxygen sensor employed as the air/fuel ratio detector 20 in the system of FIG. 1. This element 30 is of the type disclosed in the aforementioned U.S. Pat. No. 4,207,159.

A structurally basic member of this oxygen-sensitive element 30 is a substrate 32 made of a ceramic material such as alumina. A heater element 34 is embedded in the alumina substrate 32 because the oxygen-sensitive element 30 exhibits its proper function only when maintained at sufficiently elevated temperatures, e.g. at temperatures above about 500° C. In practice, the alumina substrate 32 is obtained by face-to-face bonding of two alumina sheets, one of which is provided with the heater element 34 in the form of, for example, a platinum layer of a suitable pattern.

An electrode layer 36 is formed on one side of the substrate 32, and, on the same side, a layer 38 of an oxygen ion conductive solid electrolyte such as $ZrO_2$ stabilized with CaO or $Y_2O_3$ is formed so as to cover substantially the entire area of the electrode layer 36. Another electrode layer 40 is formed on the outer surface of the solid electrolyte layer 38. Platinum is a typical example of electronically conducting materials for the inner and outer electrode layers 36 and 40.

Each of these three layers 36, 38, 40 is a thin, film-like layer (though a "thick layer" in the sense of the current electronic technology), so that the total thickness of these three layers is only about 20 μm by way of example. Macroscopically the inner electrode layer 36 is completely shielded from an environmental atmosphere by the substrate 32 and the solid electrolyte layer 38. However, both the solid electrolyte layer 38 and the outer electrode layer 40 (the inner electrode layer 36 too) are microscopically porous and permeable to gas molecules. As is known, these three layers 36, 38, 40 constitute an oxygen concentration cell which generates an electromotive force when there is a difference in oxygen partial pressure between the inner electrode side and the outer electrode side of the solid electrolyte layer 38. This element 30 is so designed as to establish a reference oxygen partial pressure at the interface between the inner electrode layer 36 and the solid electrolyte layer 38 by externally supplying a DC current to the concentration cell so as to flow through the solid electrode layer 38 between the two electrode layers 36 and 40, while the outer electrode layer 40 is exposed to a gas subject to measurement such as an exhaust gas flowing through the exhaust passage 14 in FIG. 1. Accordingly the inner electrode 36 will be referred to as reference electrode layer and the outer electrode layer 40 as measurement electrode layer.

Attached to the substrate 32 are three lead terminals 42, 44 and 46. The reference electrode layer 36 is electrically connected to the lead terminal 42 either directly or via a lead 37, and the measurement electrode layer 40 is electrically connected to the lead terminal 44 either directly or via a lead 41. The heater element 34 is connected to the lead terminals 44 and 46 either directly or via leads 33, 35, so that the lead terminal 44 serves as a ground terminal common to the heater 34 and the oxygen concentration cell of the element 30. The aforementioned DC current is supplied to the oxygen concentration cell so as to flow from the lead terminal 42 to the ground lead terminal 44 through the solid electrolyte layer 38, and an electromotive force generated by the oxygen concentration cell is measured between these two lead terminals 42 and 44.

As a practical device, the oxygen-sensitive element 30 is substantially entirely covered with a gas permeably porous protective layer 48 of a ceramic material, such as alumina, spinel or calcium zirconate.

The principle of the function of this oxygen-sensitive element 30 has already been described in this specification.

Figure 3:
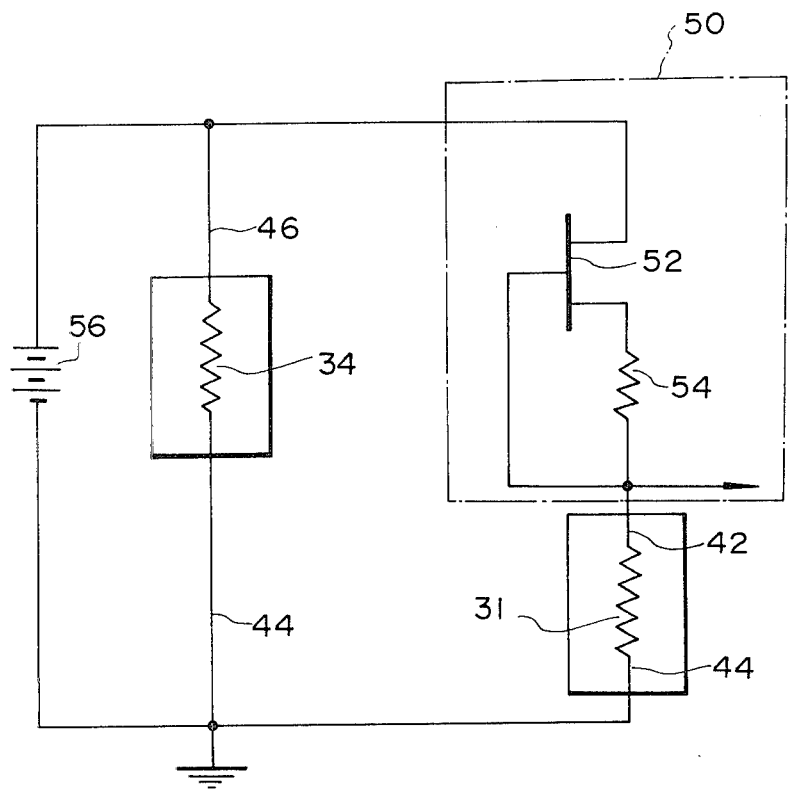
FIG. 3 is a circuit diagram showing a conventional circuit to supply a constant DC current to the sensitive part of the oxygen-sensitive element of FIG. 2 and a heating current to a heater provided to the same oxygen-sensitive element.

FIG. 3 shows a current-supplying circuit hitherto used as part of a control unit corresponding to the unit 22 in FIG. 1 to supply a heating current to the heater 34 in the oxygen-sensitive element 30 of FIG. 2 and a constant DC current to the oxygen concentration cell (in FIG. 3 represented by a resistance 31) of the same element 30.

The heating current is supplied to the heater 38 directly from a DC power source 56 such as a battery through usual resistors and a main switch (omitted from illustration).

A constant-current producing part 50 of this current-supplying circuit is constituted of an field-effect transistor 52 and a resistor 54 in a well known manner. The source of the FET 52 is connected to the positive terminal of the power source 56, and the drain is connected to the lead terminal 42 of the oxygen-sensitive element 30 through the resistor 54, so that a constant DC current is forced to flow through the oxygen concentration cell 31 from the reference electrode layer 36 toward the measurement electrode layer 40 even if certain changes occur in the internal resistance of the cell 31. Of course, the intensity of the current supplied from this circuit to the cell 31 does not vary even though the oxygen concentration in the exhaust gas varies considerably.

Figure 4:
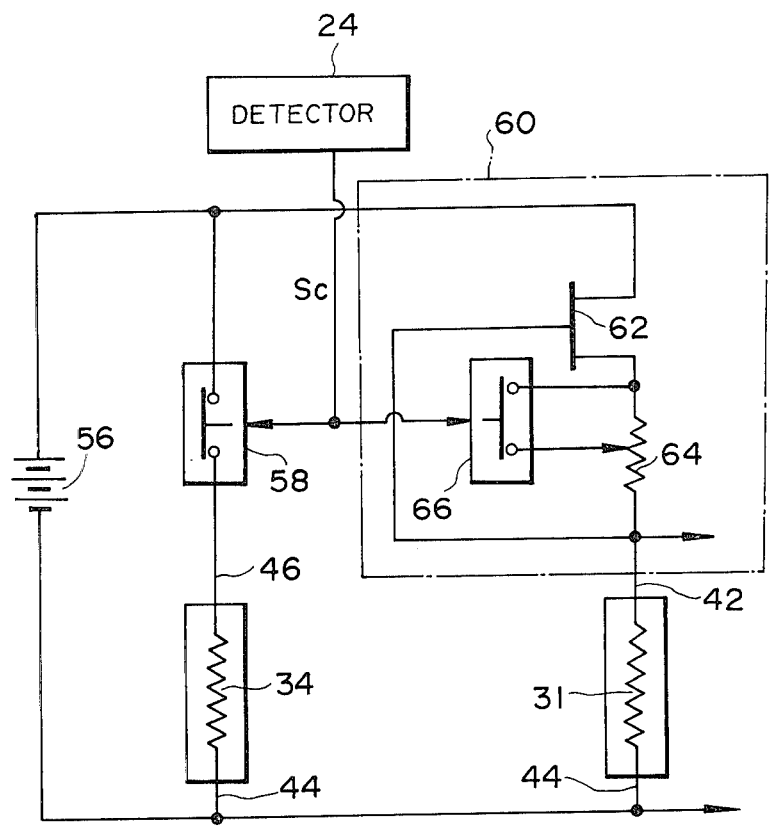
FIG. 4 is a circuit diagram showing a fundamental construction of a current control system for the oxygen-sensitive element of FIG. 2 in the system of FIG. 1, as an embodiment of the present invention.

FIG. 4 shows an embodiment of a current-supply control system according to the invention, which is incorporated in the control unit 22 of FIG. 1. As can be seen, this system is based on the current-supplying circuit of FIG. 3. As a first modification, an electrically controllable first switch 58 such as an electromagnetic relay or a switching transistor is provided between the power source 56 and the heater 34 of the oxygen-sensitive element 30. This switch 58 is normally in the on-state to establish connection of the heater 34 with the power source 56 but shifts to the off-state when the operating condition detection means 24 in FIG. 1 provides a command signal $S_c$ to this switch 58, possibly via a signal-treating circuit (not shown), to disconnect the heater 34 from the power source 56.

The command signal $S_c$ is provided when the operating condition detecting means 24 detects that the feedback control of the air/fuel ratio is discontinued and that the engine 10 is operated under a considerably high-load condition with the supply of a mixture having an air/fuel ratio considerably higher than the stoichiometric ratio. Discontinuance of the feedback control can be detected by monitoring the mode of the fuel feed rate control signal provided by the control unit 22. The detection of a high-load operating condition can be achieved by detecting or examining at least one parameter of the engine operating conditions, which may be the degree of opening of a throttle valve, magnitude of intake vacuum, rate of air intake, state of a fuel injection control signal such as the durations of individual pulses of a pulse signal, state of function of fuel injection valves and/or rotational speed of the engine. Also, the vehicle speed may be detected as a supplementary parameter. Also would be detected an unintentional condition where the fuel feed rate control signal continues to imply increasing the rate of fuel feed for an unduly long period of time.

A current-intensity control part 60 in the system of FIG. 4 is a modification of the constant-current producing part 50 in the circuit of FIG. 3. There is a field-effect transistor 62 corresponding to the FET 52 in FIG. 3 with its source connected to the power source 56, and the drain of this FET 62 is connected to the lead terminal 42 and accordingly to the concentration cell 31 of the oxygen-sensitive element 30 through a variable resistor 64 in place of the fixed resistor 54 in FIG. 3. In addition, an electrically controllable second switch 66 such as an electromagnetic relay or a switching transistor is connected with the variable resistor 64 such that the resistance of this resistor 64 decreases by a definite value when the second switch 66 takes the on-state. Alternatively, the variable resistor 64 may be replaced by two series-connected resistors with the switch 66 connected such that one of the two resistors becomes short-circuited when the switch 66 is in the on-state.

The second switch 66 is normally in the off-state, so that a current of an initially determined intensity is constantly supplied to the concentration cell 31. However, this switch 66 too is responsive to the above described command signal $S_c$ and takes the on-state while the command signal $S_c$ is produced, that is, while the engine is operating under a high-load, low air/fuel ratio condition. Then the resistance of the variable resistor 64 decreases as mentioned above, and the intensity of the current still forced to flow in the concentration cell 31 from the reference electrode 36 toward the measurement electrode 40 increases correspondingly.

As described hereinbefore, an increase in the intensity of the current flowing in the solid electrolyte layer 38 of the concentration cell 31 toward the measurement electrode layer 40 causes augmentation of the migration of oxygen ions through this solid electrolyte layer 38 toward the reference electrode layer 36, so that there appears an increasing tendency in the magnitude of the reference oxygen partial pressure on the reference electrode side. Accordingly, by adequately determining the value of the resistance to be subtracted from the total resistance of the resistor 64 by the function of the switch 66 it becomes possible to maintain the magnitude of the reference oxygen partial pressure unchanged from the initially intended level during operation of the engine under a condition represented by the presence of the command signal $S_c$ by combined effects of the interruption of the supply of the heating current to the heater 34 and the increase in the intensity of the current flowing in the cell 31.

Upon disappearance of the command signal $S_c$, the first switch 58 resumes the on-state and the second switch 66 resumes the off-state, so that the supply of the heating current to the heater 34 is resumed and the intensity of the current for the cell 31 is reverted to the initial predetermined intensity.

The oxygen-sensitive element 30 of FIG. 2 can be used also for detection of a non-stoichiometric air/fuel ratio, either higher or lower than the stoichiometric ratio, by adequately determining the intensity of a DC current forced to flow in the solid electrolyte layer 38. In the above described embodiment of the invention the aim of feedback control of air/fuel ratio was a stoichiometric ratio. However, the invention is applicable also to analogous air/fuel ratio control systems designed to maintain a predetermined non-stoichiometric air/fuel ratio by using an oxygen-sensitive element of the type as shown in FIG. 2.

The oxygen-sensitive element 30 of FIG. 2 can be operated also by forcing a constant DC current to flow in the solid electrolyte layer 38 from the measurement electrode layer 40 toward the reference electrode layer 36. The concept of the present invention regarding the temporary change of the intensity of the current for establishment of a reference oxygen partial pressure is useful also when this element 30 is operated with a current flowing from the measurement electrode 40 toward the reference electrode 36. In such a case, the herein described characteristic of the current-intensity control circuit 60 should be inversed.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A system for feedback control of the air/fuel ratio of an air-fuel mixture supplied to an internal combustion engine, the control system comprising:
   an electrically controllable fuel supplying means provided in the intake system of the engine;
   an air/fuel ratio detector which is disposed in an exhaust passage for the engine and has an oxygen-sensitive element of a concentration cell type comprising a substrate, a microscopically porous reference electrode layer formed on the substrate, a microscopically porous layer of an oxygen ion conductive solid electrolyte formed on the substrate so as to cover the reference electrode layer substantially entirely and a microscopically porous measurement electrode layer formed on the solid electrolyte layer and an electric heater;
   fuel feed control means for providing a control signal to the fuel supplying means to control the rate of fuel feed to the engine so as to maintain a predetermined air/fuel ratio by utilizing the output of the air/fuel ratio detector as a feedback signal; and
   a sub-system to supply a heating current to the heater of the air/fuel ratio detector and force a DC current of a predetermined intensity to flow through the solid electrolyte layer of the oxygen-sensitive element from the reference electrode layer toward the measurement electrode layer to cause migration of oxygen ions through the solid electrolyte layer from the measurement electrode layer toward the reference electrode layer to thereby establish a reference oxygen partial pressure at the interface between the reference electrode layer and the solid electrolyte layer,
   said sub-system comprising operating condition detecting means for producing a command signal while the operation of the fuel feed control means is temporarily discontinued to release the air/fuel ratio from the feedback control and the engine is operated under such a condition as causes a significant lowering of the concentration of oxygen in the exhaust gas, and an electrically controllable switch means for interrupting the supply of said heating current to said heater while the operating condition detecting means produces said command signal, whereby the activity of the solid electrolyte layer in the oxygen-sensitive element decreases while said command signal is produced thereby preventing significant lowering of said reference oxygen partial pressure from a predetermined level by the influence of the lowered oxygen concentration in the exhaust gas.

2. A feedback control system according to claim 1, wherein said sub-system comprises current-intensity control means for increasing the intensity of said DC current flowing through the solid electrolyte layer from said predetermined intensity while the operating condition detecting means produces said command signal for thereby augmenting the migration of oxygen ions through the solid electrolyte layer toward the reference electrode layer.

3. A feedback control system according to claims 1 or 2, wherein the operating condition detecting means has the function of detecting at least one of the degree of opening of a throttle valve provided in an induction passage for the engine, the magnitude of intake vacuum for the engine, the flow rate of air drawn into the engine, rotational speed of the engine, actual state of the function of the fuel supplying means and actual state of a signal for controlling the function of the fuel supplying means.

4. A feedback control system according to claim 2, wherein the current-intensity control means comprises a variable resistance which is connected in series with the solid electrolyte layer of the oxygen-sensitive element to determine said predetermined intensity of the current forced to flow through the solid electrolyte layer and an electrically controllable switch means connected with said resistance for short-circuiting a part of said resistance while the operating condition detecting means produces said command signal.

5. A feedback control system according to claim 1, wherein said heater is embedded in said substrate of the oxygen-sensitive element.

6. A feedback control system according to claim 1, wherein said predetermined air/fuel ratio is a stoichiometric air/fuel ratio.

* * * * *